(12) United States Patent
Liu et al.

(10) Patent No.: US 9,775,721 B2
(45) Date of Patent: Oct. 3, 2017

(54) RESORBABLE INTERBODY DEVICE

(71) Applicant: Bio2 Technologies, Inc., Woburn, MA (US)

(72) Inventors: James Jenq Liu, Mason, OH (US);
Casey S. Lewis, Medford, MA (US);
Janet L. Krevolin, Cambridge, MA (US)

(73) Assignee: BIO2 TECHNOLOGIES, INC., Woburn, MA (US)

( * ) Notice: Subject to any disclaimer, the term of this patent is extended or adjusted under 35 U.S.C. 154(b) by 372 days.

(21) Appl. No.: 14/444,262

(22) Filed: Jul. 28, 2014

(65) Prior Publication Data
US 2015/0073556 A1 Mar. 12, 2015

Related U.S. Application Data

(63) Continuation-in-part of application No. 13/678,644, filed on Nov. 16, 2012, now Pat. No. 8,790,682,
(Continued)

(51) Int. Cl.
*A61F 2/44* (2006.01)
*A61L 27/10* (2006.01)
(Continued)

(52) U.S. Cl.
CPC .............. *A61F 2/447* (2013.01); *A61F 2/28* (2013.01); *A61F 2/3094* (2013.01); *A61F 2/44* (2013.01); *A61L 27/10* (2013.01); *A61L 27/56* (2013.01); *A61L 27/58* (2013.01); *C03C 4/0014* (2013.01); *C03C 11/00* (2013.01); *A61F 2/4465* (2013.01); *A61F 2002/30062* (2013.01);
(Continued)

(58) Field of Classification Search
CPC .................. A61F 2/4455; A61F 2002/4495
USPC ............................ 623/17.11–17.16; 606/279
See application file for complete search history.

(56) References Cited

U.S. PATENT DOCUMENTS

| | | |
|---|---|---|
| 4,604,097 A | 8/1986 | Graves, Jr. et al. |
| 4,655,777 A | 4/1987 | Dunn et al. |

(Continued)

FOREIGN PATENT DOCUMENTS

| | | | |
|---|---|---|---|
| EP | 0051955 | | 5/1982 |
| GB | WO 2007/144662 | * | 12/2007 |

(Continued)

OTHER PUBLICATIONS

Hench, Larry L., et al., "Bioactive Materials for Tissue Engineering Scaffolds", In "Future Strategies for Tissue and Organ Replacement" edited by Polak, Julia M., et al., 1st ed., *World Scientific Publishing Co.*, Chapt. 1,(Aug. 2002), 1-24.

(Continued)

*Primary Examiner* — Matthew Lawson
(74) *Attorney, Agent, or Firm* — Arthur J. O'Dea

(57) ABSTRACT

A spinal interbody device fabricated of fully resorbable bioactive glass materials is used to maintain the intervertebral spacing in a fusion of adjacent vertebrae. The spinal interbody device can include regions of porous material having various levels of bioactivity so that fusion through ingrowth of bone tissue can be provided while regions of the spinal interbody device can continue to maintain the intervertebral space.

21 Claims, 3 Drawing Sheets

Related U.S. Application Data which is a continuation of application No. 12/832,391, filed on Jul. 8, 2010, now Pat. No. 8,337,876.

(60) Provisional application No. 61/861,793, filed on Aug. 2, 2013, provisional application No. 61/224,675, filed on Jul. 10, 2009, provisional application No. 61/234,768, filed on Aug. 18, 2009.

(51) Int. Cl.
 *A61L 27/58* (2006.01)
 *A61L 27/56* (2006.01)
 *A61F 2/28* (2006.01)
 *A61F 2/30* (2006.01)
 *C03C 4/00* (2006.01)
 *C03C 11/00* (2006.01)

(52) U.S. Cl.
 CPC ............ *A61F 2002/3092* (2013.01); *A61F 2002/30904* (2013.01); *A61F 2002/30968* (2013.01); *A61F 2002/4495* (2013.01); *A61F 2310/00179* (2013.01); *A61F 2310/00293* (2013.01); *A61F 2310/00329* (2013.01); *A61L 2400/18* (2013.01); *A61L 2430/38* (2013.01)

(56) References Cited

U.S. PATENT DOCUMENTS

| | | | |
|---|---|---|---|
| 5,009,822 A | 4/1991 | Sacks et al. | |
| 5,236,458 A | 8/1993 | Ducheyne et al. | |
| 5,397,365 A | 3/1995 | Trentacosta | |
| 5,419,857 A | 5/1995 | Van den Sype | |
| 5,468,544 A | 11/1995 | Marcolongo et al. | |
| 5,629,186 A | 5/1997 | Yasukawa et al. | |
| 5,676,720 A | 10/1997 | Ducheyne et al. | |
| 5,721,049 A | 2/1998 | Marcolongo et al. | |
| 6,027,684 A | 2/2000 | Gheorghiu et al. | |
| 6,048,199 A | 4/2000 | Dull | |
| 6,089,860 A | 7/2000 | Dull | |
| 6,146,892 A | 11/2000 | Ma et al. | |
| 6,149,688 A | 11/2000 | Brosnahan et al. | |
| 6,162,537 A | 12/2000 | Martin et al. | |
| 6,187,329 B1 | 2/2001 | Agrawal et al. | |
| 6,240,926 B1 | 6/2001 | Chin Gan et al. | |
| 6,277,394 B1 | 8/2001 | Sierra | |
| 6,296,667 B1 | 10/2001 | Johnson et al. | |
| 6,325,963 B1 | 12/2001 | Dull | |
| 6,406,498 B1 | 6/2002 | Tormala et al. | |
| 6,451,059 B1 | 9/2002 | Janas et al. | |
| 6,471,993 B1 | 10/2002 | Shastri et al. | |
| 6,626,950 B2 | 9/2003 | Brown et al. | |
| 6,696,073 B2 | 2/2004 | Boyce et al. | |
| 7,005,135 B2 | 2/2006 | Janas et al. | |
| 7,166,133 B2 | 1/2007 | Evans et al. | |
| 7,235,107 B2 | 6/2007 | Evans et al. | |
| 7,241,316 B2 | 7/2007 | Evans et al. | |
| 7,241,486 B2 | 7/2007 | Pirhonen | |
| 7,270,813 B2 | 9/2007 | Shimp et al. | |
| 7,767,221 B2 | 8/2010 | Lu et al. | |
| 8,093,166 B2 | 1/2012 | Moimas et al. | |
| 8,287,896 B2 | 10/2012 | Jung et al. | |
| 2001/0041325 A1 | 11/2001 | Ylanen et al. | |
| 2002/0160175 A1 | 10/2002 | Pirhonen | |
| 2003/0125739 A1* | 7/2003 | Bagga ................ | A61F 2/4455 606/247 |
| 2003/0147860 A1 | 8/2003 | Marchosky | |
| 2004/0006153 A1 | 1/2004 | Seppala et al. | |
| 2004/0009598 A1 | 1/2004 | Hench et al. | |
| 2005/0037978 A1 | 2/2005 | Damien | |
| 2005/0081750 A1 | 4/2005 | Xu et al. | |
| 2005/0118236 A1 | 6/2005 | Qiu et al. | |
| 2005/0147642 A1 | 7/2005 | Laredo et al. | |
| 2006/0093645 A1 | 5/2006 | Janas et al. | |
| 2006/0216321 A1 | 9/2006 | Lyu et al. | |
| 2007/0055373 A1 | 3/2007 | Hudgins et al. | |
| 2007/0087059 A1 | 4/2007 | Everaerts et al. | |
| 2007/0098799 A1 | 5/2007 | Zhang et al. | |
| 2007/0107395 A1 | 5/2007 | Zuberi et al. | |
| 2007/0110819 A1 | 5/2007 | Pastorello et al. | |
| 2007/0123984 A1 | 5/2007 | Hodorek | |
| 2007/0162151 A1 | 7/2007 | Chang et al. | |
| 2007/0190108 A1 | 8/2007 | Datta et al. | |
| 2008/0081061 A1 | 4/2008 | King et al. | |
| 2008/0103605 A1 | 5/2008 | Kadiyala et al. | |
| 2008/0152687 A1 | 6/2008 | Thorne | |
| 2008/0154379 A1* | 6/2008 | Steiner ................ | A61F 2/4455 623/17.16 |
| 2008/0286179 A1 | 11/2008 | Liu et al. | |
| 2009/0035511 A1 | 2/2009 | Liu et al. | |
| 2010/0168798 A1* | 7/2010 | Clineff ................ | A61L 27/446 606/279 |
| 2010/0179667 A1 | 7/2010 | Day et al. | |
| 2011/0106255 A1 | 5/2011 | Liu et al. | |
| 2011/0106272 A1 | 5/2011 | Liu | |
| 2013/0297038 A1* | 11/2013 | McKay ................ | A61F 2/28 623/23.57 |

FOREIGN PATENT DOCUMENTS

| | | |
|---|---|---|
| WO | WO-86/04088 | 7/1986 |
| WO | WO-01/32072 | 5/2001 |
| WO | WO-01/73126 | 10/2001 |
| WO | 2004-098456 | 11/2004 |
| WO | WO-2006/118554 | 11/2006 |

OTHER PUBLICATIONS

Liebschner, M.A.K. et al., "Optimization of Bone Scaffold Engineering for Load Bearing Applications", *Topics in Tissue Engineering* 2003, Chapter 6,(2003).

Brown, Roger F., et al., "Growth and differentiation of osteoblastic cells on 13-93 bioactive glass fibers and scaffolds", *Acta Biomaterialia* 4, (2008),387-396.

Moimas, Loredana et al., "Rabbit pilot study on the resorbability of three-dimensional bioactive glass fibre scaffolds", *Acta Biomaterialia* 2, (2006), 191-199.

Barthelat, Francois "Biomimetics for next generation materials", *Phil. Trans R. Soc. A*, 365,(2007),2907-2919.

Brink, Maria et al., "Compositional dependence of bioactivity of glasses in the system $Na_2O$—$K_2O$—$MgO$—$CaO$—$B_2O_3$—$P_2O_5$—$SiO_2$", *J Biomed Mater Res*, 37,(1997),114-121.

Brink, Maria "The influence of alkali and alkaline earths on the working range for bioactive glasses", *Journal of Biomedical Materials Research*, vol. 36,(1997),109-117.

Karlsson, KAJ H., et al., "Thirty-five years of guided tissue engineering", *Journal of Non-Crystalline Solids*, 354,(2008),717-721.

Itala, A et al., "Characterization of microrough bioactive glass surface: Surface reactions and osteoblast responses in vitro", *J Biomed Mater Res*, 62,(2002),404-411.

Vedel, Erik "Predicting the Properties of Bioactive Glasses", *Abo Akademi University, Laboratory of Inorganic Chemistry, Academic Dissertation*, Report 08-01,(2008).

Arstila, Hanna et al., "Factors affecting crystallization of bioactive glasses", *Journal of the European Ceramic Society*, 27,(2007), 1543-1546.

Fu, Qiang et al., "Freeze Casting of Porous Hydroxyapatite Scaffolds. II. Sintering, Microstructure, and Mechanical Behavior", *J Biomed Mater Res*, Part B: Appl Biomater 86B,(2008),514-522.

Fu, Qiang et al., "In vitro cellular response to hydroxapatite scaffolds with oriented pore architectures", *Materials Science and Engineering* C, MSC-02642,(2009).

Fu, Qiang et al., "Mechanical and in vitro performance of 13-93 bioactive glass scaffolds prepared by a polymer foam replication technique", *Acta Biomaterialia*, 4,(2008),1854-1864.

\* cited by examiner

RESORBABLE INTERBODY DEVICE

CROSS-REFERENCE TO RELATED APPLICATIONS

This application is a continuation-in-part of U.S. patent application Ser. No. 13/678,644 filed Nov. 16, 2012 which is a continuation of U.S. application Ser. No. 12/832,391 filed Jul. 8, 2010, now issued as U.S. Pat. No. 8,337,876, which claims the benefit of U.S. Provisional Patent Application Nos. 61/224,675 filed Jul. 10, 2009 and 61/234,768 filed Aug. 18, 2009, each incorporated herein by reference. This application claims the benefit of U.S. Provisional Patent Application No. 61/861,793 filed Aug. 2, 2013, incorporated herein by reference.

FIELD OF THE INVENTION

The present invention relates generally to a spinal interbody device such as that used in lumbar or cervical spine fusion procedures, and specifically relates to an interbody device that resorbs over time.

BACKGROUND OF THE INVENTION

Spinal interbody devices are common in spine procedures today. These devices encompass many products in the marketplace. Implants are constructed from PEEK, titanium and various other materials and have been designed for insertion through anterior, posterior and lateral approaches. Typically, interbody devices require additional fixation to create a fusion across the intended vertebral level. In lumbar surgery, this supplemental fixation can include an anterior plate or pedicle screws and rods inserted posteriorly in a 360° procedure.

Spinal interbody devices are used in lumbar or cervical spine fusion procedures to treat spondylolisthesis and degenerative disc disease, among others. In this procedure the device is inserted between adjacent vertebrae, typically with bone graft materials, to maintain the intervertebral space during the intervening period upon which bone fusion occurs between the adjacent vertebrae.

While existing spinal interbody devices are suitable for their intended purposes, improvements may be made. In particular, it is desirable to have a spinal interbody device that may be readily and harmlessly resorbed while bone ingrowth occurs fusing the adjacent vertebrae subsequent to the spinal procedure.

BRIEF SUMMARY OF THE INVENTION

The present invention meets the objectives of providing a resorbable spinal interbody device to maintain the intervertebral space and promoting bone tissue ingrowth to effectuate fusion. The resorbable spinal interbody device can be implanted in a lumbar or cervical spine fusion procedure with or without fixation due to the load bearing strength and high rate of bioactivity exhibited by the bioactive glass and glass-ceramic compositions.

BRIEF DESCRIPTION OF THE SEVERAL VIEWS OF THE DRAWINGS

The foregoing and other objects, features, and advantages of the invention will be apparent from the following detailed description of the several embodiments of the invention as illustrated in the accompanying drawings in which like reference characters refer to the same parts throughout the different views. The drawings are not necessarily to scale, with emphasis instead being placed upon illustrating the principles of the invention.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION OF THE INVENTION

The present invention provides a resorbable spinal interbody device that can be implanted between adjacent vertebrae to maintain the intervertebral space while bone ingrowth through and around the resorbable interbody device ultimately fuses the adjacent vertebra. The present invention exhibits a controlled resorbability over time to allow the newly formed bone to gradually assume the spine load. Ultimately once the adjacent vertebrae are fused the interbody device can be fully resorbed by the patient with no harmful side effects.

Figure 1:
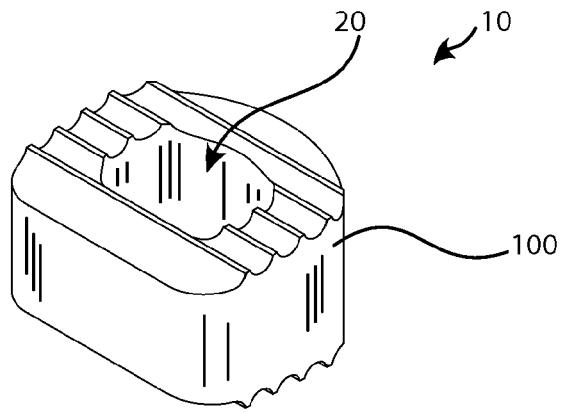
FIG. 1 shows a first spinal interbody device according to an embodiment of the present invention.

Referring to FIG. 1, in a first exemplary embodiment a spinal interbody device 10 is shown for use in fusion of adjacent vertebrae to maintain the intervertebral spacing as bone tissue fuses the adjacent vertebrae.

In an embodiment described with reference to FIG. 1, the interbody device 10 has a structural region 100 composed of bioactive glass or bioactive glass-ceramic that maintains the intervertebral space once implanted and can provide load bearing strength.

Glass-ceramic materials exhibit properties of increased strength, toughness, thermal stability, machinability over amorphous glass materials. A glass-ceramic biomaterial can be designed to exhibit specific rates of dissolution and resorption in vivo. For example, wollastonite in a bioactive glass matrix as a glass-ceramic composition can exhibit bioactivity and bioresorption when implanted in living tissue. The present invention relates to the formation of glass-ceramic compositions while retaining a porous, osteostimulative microstructure.

The structural region 100 of the interbody device of the present invention can be fabricated using fibers as a raw material that create a bioactive glass-ceramic composition that has a substantially uniform glass-ceramic composition throughout the porous structure. In this way a bioactive and resorbable device can be fabricated with increased strength and durability provided by the ceramic phase of the material. The fibers can be composed of a material that is a precursor to the glass-ceramic material, and in an embodiment the fiber is a silica calcium phosphate glass. The term "fiber" as used herein is meant to describe a filament or elongated member in a continuous or discontinuous form having an aspect ratio greater than one, and formed from a fiber-forming process such as drawn, spun, blown, or other similar process typically used in the formation of fibrous materials or other high aspect-ratio materials.

Bioactive materials, such as silica- or phosphate-based glass materials with certain compositional modifiers that result in bioactivity, including but not limited to modifiers such as oxides of magnesium, sodium, potassium, calcium, phosphorus, and boron exhibit a narrow working range because the modifiers effectively reduce the devitrification temperature of the bioactive material. The working range of a glass material is typically known to be the range of temperatures at which the material softens such that it can be readily formed. In a glass fiber forming process, the glass material in a billet or frit form is typically heated to a temperature in the working range upon which the glass material is molten and can be drawn or blown into a continuous or discontinuous fiber. The working range of bioactive glass materials is inherently narrow since the devitrification temperature of the glass material is either extremely close or within the working range of the material. In other words, in a typical process for the formation of fiber-based bioactive glass compositions, the temperature at which a fiber can be drawn, blown, or otherwise formed, is above the glass transition temperature but less than the devitrification temperature of the bioactive glass composition. When certain bioactive glass materials are drawn or blown into a fiber form at or near the devitrification temperature, the molten or softened glass undergoes a phase change through crystallization that inhibits the continuous formation of fiber.

Figure 5:
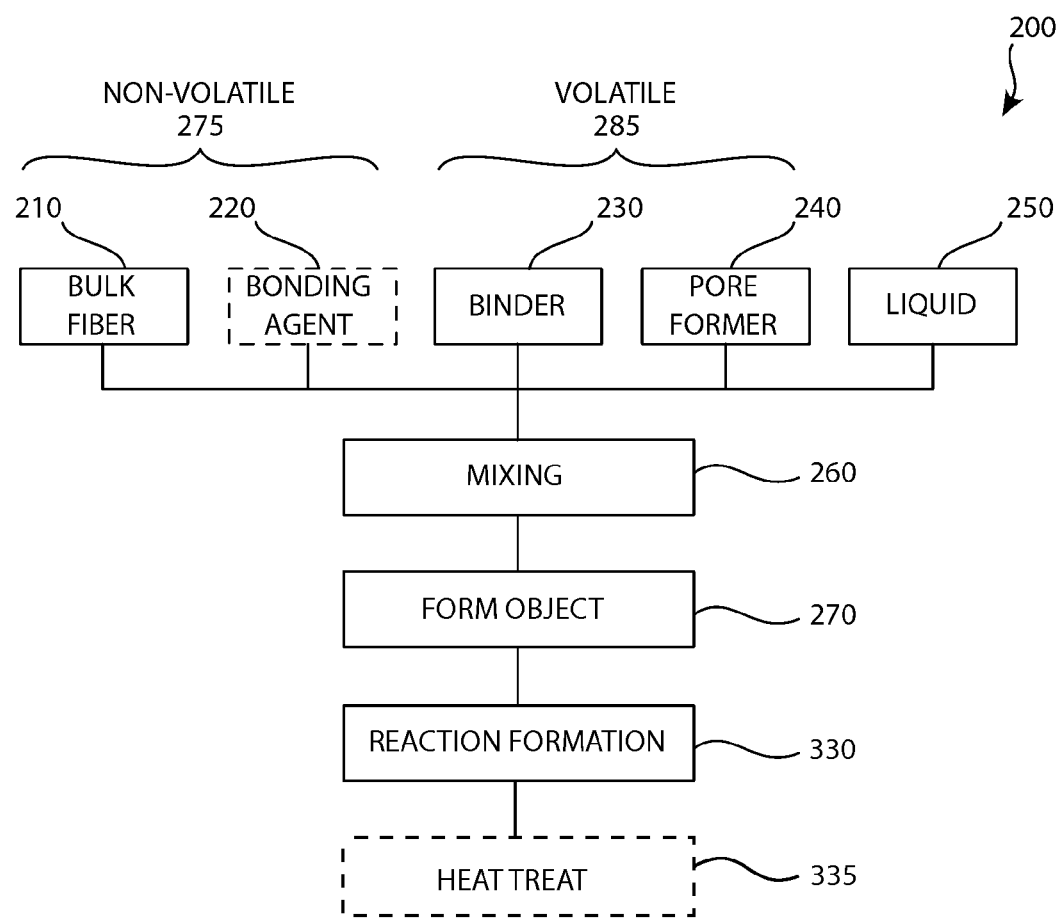
FIG. 5 shows a method used to fabricate a porous structural region of the spinal interbody device of the present invention.

FIG. 5 depicts the method 200 of the present invention to fabricate the structural region 100 having a bioactive glass-ceramic composition. Generally, amorphous glass fiber 210 is mixed with a binder 230, a pore former 240, and a liquid 250 to form a plastically moldable material which is then reaction formed into a glass-ceramic composition to form the porous structure. A subsequent heat treating process is provided to continue the controlled crystallization of the porous structure into the desired glass-ceramic composition.

The fibers 210 can be provided in bulk form, or as chopped fibers in a composition that is a bioactive glass material. A fiber 210 that is a bioactive glass material includes a fiber having a composition that is at least the components of the desired bioactive glass-ceramic composition. For example, the fiber 210 can be a silica calcium phosphate fiber, or it can be a silica calcium fiber, or a combination of any of the compositions used to form the desired bioactive glass-ceramic composition. The diameter of the fiber 210 can range from about 1 to about 200 μm and typically between about 5 to about 100 μm. Fibers 210 of this type can be produced with a relatively narrow and controlled distribution of fiber diameters or, depending upon the method used to fabricate the fiber, a relatively broad distribution of fiber diameters can be produced. Fibers 210 of a given diameter may be used or a mixture of fibers having a range of fiber diameters can be used. The diameter and length of the fibers 210 will influence the resulting pore size, pore size distribution, strength, and elastic modulus of the structural region 100, that will influence not only the osteoconductivity of the structural region 100, but also the rate at which the porous structure is dissolved by body fluids when implanted in living tissue and the resulting strength characteristics, including compressive strength and elastic modulus.

The fibers 210 used according to the present invention as herein described are typically continuous and/or chopped glass fiber. As described herein above certain bioactive glass compositions are difficult to form as a fiber because the working range of the material is extremely narrow. Silica glass in various compositions can be readily drawn into continuous or discontinuous fiber but the addition of calcium oxide and/or phosphate compounds necessary to create a silica-based bioactive composition are the very compounds that result in the reduction of the working range of the silica-based glass. The use of a fiber 210 that has a composition that is a precursor to the desired bioactive glass-ceramic composition provides for a readily-obtained and easily formed fiber material to form a porous fiber-based structure that is crystallized into the desired bioactive composition during the formation of the tissue scaffold.

Examples of fiber 210 that can be used according to the present invention include silica-based glass fiber. Silica-based materials having a calcium oxide content less than 30% by weight can be typically drawn or blown into fiber form. Silica-based glass materials are generally required to have an alumina content less than 2% by weight since any amount of alumina in excess of that amount will reduce the bioactive characteristics of the resulting structure. Phosphate glasses are precursors to bioactive compositions and can be readily provided in fiber form. These precursor materials that exhibit a sufficient working range can be made into a fiber form through melting in any one of various methods. An exemplary method involves a combination of centrifugal spinning and gaseous attenuation. A glass stream of the appropriate viscosity flows continuously from a furnace onto a spinner plate rotating at thousands of revolutions per minute. Centrifugal forces project the glass outward to the spinner walls containing thousands of holes. Glass passes through the holes, again driven by centrifugal force, and is attenuated by a blast of heated gas before being collected. In another exemplary method, glass in a molten state is heated in a vessel perforated by one or more holes of a given diameter. The molten glass flows and is drawn through these holes, forming individual fibers. The fibers are merged into strands and collected on a mandrel.

Alternative fiber and fiber-like materials that are precursors to bioactive glass-ceramic compositions can be used. For example, a sol-gel fiber drawing method pulls or extrudes a sol-gel solution of the precursor with the appropriate viscosity into a fiber strand that is subsequently heat treated to bind the material into a cohesive fiber. The sol-gel fiber can be formed from a precursor material or a combination of one or more precursor materials that react with each other to create the desired bioactive glass-ceramic composition at the reaction formation 330 step, as described in further detail below. Yet other alternative methods can be used to provide a fiber 210. For example, whiskers and fiber-like segments of silica-based oxides of magnesium, sodium, potassium, calcium, and phosphorus can be provided as the fiber 210.

The binder 230 and the liquid 250, when mixed with the fiber 210, and pore former 240 create a plastically formable batch mixture that enables the fibers 210 to be evenly distributed throughout the batch, while providing green strength to permit the batch material to be formed into the desired shape in the subsequent forming step 270. An organic binder material can be used as the binder 230, such as methylcellulose, hydroxypropyl methylcellulose (HPMC), ethylcellulose and combinations thereof. The binder 230 can include materials such as polyethylene, polypropylene, polybutene, polystyrene, polyvinyl acetate, polyester, isotactic polypropylene, atactic polypropylene, polysulphone, polyacetal polymers, polymethyl methacrylate, fumaron-indane copolymer, ethylene vinyl acetate copolymer, styrene-butadiene copolymer, acryl rubber, polyvinyl butyral, inomer resin, epoxy resin, nylon, phenol formaldehyde, phenol furfural, paraffin wax, wax emulsions, microcrystalline wax, celluloses, dextrines, chlorinated hydrocarbons, refined alginates, starches, gelatins, lignins, rubbers, acrylics, bitumens, casein, gums, albumins, proteins, glycols, hydroxyethyl cellulose, sodium carboxymethyl cellulose, polyvinyl alcohol, polyvinyl pyrrolidone, polyethylene oxide, polyacrylamides, polyethyterimine, agar, agarose, molasses, dextrines, starch, lignosulfonates, lignin liquor, sodium alginate, gum arabic, xanthan gum, gum tragacanth, gum karaya, locust bean gum, irish moss, scleroglucan, acrylics, and cationic galactomanan, or combinations thereof. Although several binders 230 are listed above, it will be appreciated that other binders may be used. The binder 230 provides the desired rheology and cohesive strength of the plastic batch material in order to form a desired object and maintaining the relative position of the fibers 210 in the mixture while the object is formed, while remaining inert with respect to the bioactive materials. The physical properties of the binder 230 will influence the pore size and pore size distribution of the pore space 120 of the structural region 100. Preferably, the binder 230 is capable of thermal disintegration, or selective dissolution, without impacting the chemical composition of the bioactive components, including the fiber 210.

The liquid 250 is added as needed to attain a desired rheology in the plastic batch material suitable for forming the plastic batch material into the desired object in the subsequent forming step 270. Water is typically used though solvents of various types can be utilized. Rheological measurements can be made during the mixing step 260 to evaluate the plasticity and cohesive strength of the mixture prior to the forming step 270.

Pore formers 240 are included in the mixture to define and enhance the pore space of the structural region 100 and to provide uniform heating throughout the object during the reaction formation step 330, as described in more detail below. Generally, pore formers are non-reactive materials that occupy volume between the fibers in the plastic batch material during the mixing step 260 and the forming step 270. The particle size and size distribution of the pore former 240 influences the resulting pore size and pore size distribution of the pore space in the structural region 100. Particle sizes can typically range between about 25 μm or less to about 450 μm or more, or in the range of about 100 μm to about 600 μm, or alternatively, the particle size for the pore former can be a function of the fibers 210 diameter ranging from about 0.1 to about 100 times the diameter of the fibers 210. The pore former 240 must be readily removable during the reaction forming step 330 without significantly disrupting the relative position of the surrounding fibers 210. In an embodiment of the invention, the pore former 240 can be removed via pyrolysis or thermal degradation, or volatilization at elevated temperatures during the reaction forming step 330. For example, graphite or carbon particles can be included in the mixture as the pore former 240. Removal of the pore former during the reaction forming step 330 provides additional heat as the pore former 240 is exothermically oxidized or combusted so that a controlled heating of the glass fiber can facilitate the formation of the desired glass-ceramic composition and thus, the selection of the composition of at least a portion of the pore former 240 may be limited to those materials that provide the requisite temperature differential during heating, as described in further detail below. One skilled in the art would appreciate the availability of alternate material compositions for use as the pore former 240. Additionally, mixtures of a plurality of materials and material compositions can be selected as a pore former 240. Alternative materials include, without limitation: carbon black, activated carbon, graphite flakes, synthetic graphite, wood flour, modified starch, celluloses, coconut shell husks, latex spheres, bird seeds, saw dust, pyrolyzable polymers, poly (alkyl methacrylate), polymethyl methacrylate, polyethyl methacrylate, poly n-butyl methacrylate, polyethers, poly tetrahydrofuran, poly (1, 3-dioxolane), poly (alkalene oxides), polyethylene oxide, polypropylene oxide, methacrylate copolymers, polyisobutylene, polytrimethylene carbonate, polyethylene oxalate, polybeta-propiolactone, polydelta- valerolactone, polyethylene carbonate, polypropylene carbonate, vinyl toluene/alpha-methylstyrene copolymer, styrene/alpha-methyl styrene copolymers, and olefin-sulfur dioxide copolymers. Pore formers 240 may be generally defined as organic or inorganic, with the organic typically burning off at a lower temperature than the inorganic. Although several pore formers 240 are listed above, it will be appreciated that other pore formers 240 may be used. Pore formers 240 can be, though need not be, fully biocompatible since they are removed from the structural region 100 during processing.

Optionally, additional precursors to the desired bioactive glass- ceramic material can be provided as a bonding agent 220 to combine with the composition of the fiber 210 to modify the composition of the glass and/or ceramic phase of the resulting material. The bonding agent 220 can include powder-based material of the same composition as the bulk fiber 210, or it can include powder-based material of a different composition. In an embodiment of the invention the bonding agent 220 can be coated on the fibers 210 as a sizing or coating. In this embodiment, additional precursors to the bioactive composition are added to the fiber, for example, as a sizing or coating. In an alternate embodiment, the bonding agent 220 is a sizing or coating that is added to the fiber during or prior to the mixing step 260. The bonding agent 220 can be solids dissolved in a solvent or liquid that are deposited on the fiber and/or other bonding agent 220 precursors when the liquid or solvent is removed. The relative quantities of the fiber 210 and the bonding agent 220 combined with the heat treatment generally determine the compositions of the respective phases of glass and ceramic components of the structural region 100.

The relative quantities of the respective materials, including the bulk fiber 210, the binder 230, and the liquid 250 depend on the overall porosity desired in the structural region 100. For example, to provide a structure 100 having approximately 60% porosity, nonvolatile components 275, such as the fiber 210, would amount to approximately 40% of the mixture by volume. The relative quantity of volatile components 285, such as the binder 230 and the liquid 250 would amount to approximately 60% of the mixture by volume, with the relative quantity of binder to liquid determined by the desired rheology of the mixture. Furthermore, to produce a structure 100 having porosity enhance by the pore former 240, the amount of the volatile components 285 is adjusted to include the volatile pore former 240. Similarly, to produce a structure having strength enhanced by the bonding agent 220, the amount of the nonvolatile components 275 would be adjusted to include the nonvolatile bonding agent 220. It can be appreciated that the relative quantities of the nonvolatile components 275 and volatile components 285 and the resulting porosity of the structure 100 will vary as the material density may vary due to the reaction of the components during the reaction forming step 330. Specific examples are provided herein below.

In the mixing step 260, the fiber 210, the binder 230, the liquid 250, the pore former 240 and optionally, the bonding agent 220, if included, are mixed into a homogeneous mass of a plastically deformable and uniform mixture. The mixing step 260 may include dry mixing, wet mixing, shear mixing, and kneading, which can be necessary to evenly distribute the material into a homogeneous mass while imparting the requisite shear forces to break up and distribute or de-agglomerate the fibers 210 with the non-fiber materials. The amount of mixing, shearing, and kneading, and duration of such mixing processes depends on the selection of fibers 210 and non-fiber materials, along with the selection of the type of mixing equipment used during the mixing step 260, in order to obtain a uniform and consistent distribution of the materials within the mixture, with the desired rheological properties for forming the object in the subsequent forming step 270. Mixing can be performed using industrial mixing equipment, such as batch mixers, shear mixers, and/or kneaders. The kneading element of the mixing step 260 distributes the fiber 210 with the bonding agent 220 and the binder 230 to provide a formable batch of a homogeneous mass with the fiber being arranged in an overlapping and intertangled relationship with the remaining fiber in the batch.

The forming step 270 forms the mixture from the mixing step 260 into the object that will become the structural region 100. The forming step 270 can include extrusion, rolling, pressure casting, or shaping into nearly any desired form in order to provide a roughly shaped object that can be cured in the reaction forming step 330 to provide the structure 100. It can be appreciated that the final dimensions of the structure 100 may be different than the formed object at the forming step 270, due to expected shrinkage of the object during the reaction forming step 330, and further machining and final shaping may be necessary to meet specified dimensional requirements. In an exemplary embodiment to provide samples for mechanical and in vitro and in vivo testing, the forming step 270 extrudes the mixture into a cylindrical rod using a piston extruder forcing the mixture through a round die.

The object is then reaction formed into the glass-ceramic composition at reaction forming step 330. Here, the object is subjected to a series of heat treatments that sequentially remove the volatile components 285 without substantially disturbing the relative position of the fiber 210, as determined by the mixing step 260, the forming step 270 and the volatile components 285 including the pore former 240, and bond the fiber into a porous construct and initiating a reaction formation of the bioactive glass fiber composition into a bioactive glass-ceramic composition to provide the structural region 100.

The reaction forming step can include a drying phase to remove the liquid in an elevated temperature environment with or without forced convection. Various methods of heating the object can be used to dry the parts including, but not limited to heated air convection heating, vacuum freeze drying, solvent extraction, microwave or electromagnetic radio frequency (RF) drying methods. The liquid 250 within the formed object is preferably not removed so rapidly so as to contribute to cracks from shrinkage. Typically, for aqueous based systems, the formed object can be dried when exposed to temperatures between about 90° C. and 150° C. for about one hour, though the actual drying time may vary due to the size and shape of the formed object, with larger more massive objects taking longer to dry. In the case of microwave or RF energy drying, the liquid itself, and/or other components of the object, absorb the radiated energy to more evenly generate heat throughout the material During the drying phase of the reaction forming step 330, depending on the selection of materials used as the volatile components 285, the binder 230 can congeal or gel to provide greater green strength to provide rigidity and strength in the object for subsequent handling.

The reaction forming step 330 can include a binder removal to remove the binder 230 through pyrolysis, solvent extraction, and/or thermal degradation. For example, HPMC used as a binder 230 will thermally decompose at approximately 300° C. and a heat treatment phase holding a formed object at that temperature for approximately two hours can effectively remove the HPMC binder without disturbing the relative position of the fibers 210 in the formed object.

The reaction formation step 330 includes a bond formation phase that heats the formed object to a reaction and bond formation temperature resulting in the formation of fiber-to-fiber bonds at overlapping and adjacent nodes of the fiber structure. In the method of the present invention the temperature at which the reaction and bond formation temperature occurs exceeds the devitrification temperature of the glass composition of the fiber 210 so that a glass-ceramic composition is formed. The tendency of an amorphous glass composition to crystalize depends largely on glass composition, surface condition and heating and cooling rate. An amorphous glass, such as silica calcium phosphate 13-93, will precipitate wollastonite ($CaSiO_3$) crystals at temperatures above 800° C. when the glass is in a high surface area to mass relationship such as the fiber construct of the formed object. To ensure the homogeneous formation of wollastonite crystals in an amorphous glass matrix of the fiber structure of the present invention the bond formation phase of the reaction formation step 330 is preferably performed using a combustion of the pore former 240 to provide rapid and uniform heating throughout the volume of the formed object. The combustion of the pore former 240 in conjunction with the thermal environment during the reaction formation step 330 provides the thermal energy necessary to crystallize the fiber 210 into the desired glass-ceramic composition homogeneously throughout the internal structure of the formed object. In an embodiment of the invention greater than 50% by weight of the porous matrix is a single phase of a calcium silicate ceramic. In an alternate embodiment, greater than 40% by weight of the porous matrix is a single phase of a calcium silicate ceramic. In yet another embodiment greater than 20% by weight of the porous matrix is a single phase of a calcium silicate ceramic.

The combustion of the pore former 240 is one mechanism to provide the heating rate to initiate the formation of the glass ceramic by providing rapid and uniform heating throughout the formed object during the reaction formation step 330. The pore former 240 is preferably a combustible material such as carbon or graphite, starch, organics or polymers such as polymethyl methacrylate (PMMA), or other material that exothermically oxidizes. Generally, the pore former 240 is selected based on the temperature at which the material initiates combustion as can be determined by thermal analysis such as Thermogravimetric Analysis (TGA) or Differential Thermal Analysis (DTA) or a simultaneous combination of DTA/TGA which detects both mass loss and thermal response. For example, a DTA/

TGA analysis determines the exothermic combustion point of carbon particles to be 621° C. and graphite flakes to be 603° C. that is suitable for use with a 13-93 bioactive glass composition having a devitrification temperature of approximately 800° C.

The reaction formation step 330 provides thermal environment sufficient to convert the amorphous glass composition of the fiber 210 into a glass-ceramic composition uniformly throughout the formed body through convective heat transfer from the kiln or oven in combination with a second heating source such as the exothermic combustion of the pore former 240 and holding at a temperature exceeding the devitrification temperature of the amorphous glass composition. In this way the nucleation of ceramic phase crystal structure precipitates and grows to form a glass-ceramic composition wherein the amorphous phase and the ceramic phase are bioactive and resorbable when implanted in vivo. The glass transition temperature of the amorphous glass fiber is typically exceeded during the reaction formation step 330 as the overlapping and intertangled fiber is fused into a porous rigid matrix with the distinct structural features of the fiber material becoming diminished. As the crystalline phase precipitates the amorphous glass fuses to form the porous rigid matrix. The fiber form of the bioactive glass provides preferential ordering of the crystalline phase with less grain boundary influences compared to powder-based or particle-based raw materials. Additional control over the reaction formation step 330 can be provided through controlling the heating rate of process gas in the kiln or oven to delay or accelerate the combustion of the pore former 240. For example, air or nitrogen purge flowrates can be adjusted to control the amount of oxygen present in the processing environment to support combustion or oxidation of the pore former materials. Alternative heating modes for the kiln can include microwave heating and/or direct flame heating to provide the heating rates necessary to initiate crystallization of the ceramic phase of the porous matrix.

The bonds formed between overlapping and adjacent nodes of the fibers forming the formed object can be glass bonds having a composition substantially the same as the composition of the fiber 210. The bonds can also have the same glass-ceramic composition that forms during the reaction formation step 330. The present invention provides a bioactive and resorbable tissue scaffold device that can be fabricated using medically approved materials or fabricated into medically approved materials.

Referring still to FIG. 5 an optional heat treating step 335 is performed subsequent to the reaction formation step 330 to remove internal stress in the structure and to promote crystal growth of the ceramic phase of the glass-ceramic composition. The heat treating step 335 can be performed by heating the formed object after the reaction formation step 330 to a temperature at which the glass-ceramic material will support continued growth of the ceramic phase, such as when heated above the devitrification temperature of the composition of the amorphous glass fiber. Additionally, the heat treating step 335 can relieve internal stresses that may build up during the heating/cooling cycles in the reaction formation step 330. Heat treating the glass-ceramic material of the formed object after the reaction formation step 330 involves heating the object to a temperature that is the stress relief point of the materials, i.e., a temperature at which the glass-ceramic material is hard enough to maintain its shape and form but sufficient to relieve internal stress. The heat treating temperature is determined by the composition of the glass-ceramic material. The duration of the heat treating step 335 is determined by the relative size and mass of the object.

The heat treating step 335 includes a cooling phase that slowly cools the heat treated object at a rate that is limited by the heat capacity, thermal conductivity, and thermal expansion coefficient of the glass-ceramic material. Typically, most glass-ceramic compositions having a mass of approximately 10 grams can be heat treated in a kiln at a temperature that is approximately 50° C. less than the reaction formation temperature for four to six hours and cooled to room temperature over approximately four hours.

Alternatively, the structural region 100 can be composed of an amorphous bioactive glass composition in high strength/lower porosity form that exhibits strength sufficient to support anatomic loads in the human spine. The structural region 100 in a bioactive glass composition can be fabricated using the same method 200 described above with reference to the first exemplary embodiment of FIG. 1 with specific modifications to the process to ensure the formed object maintains the amorphous glass composition of the bioactive fiber 200. A first modification to the process of the method 200 can be implemented by reducing or eliminating the use of a poreformer 240 that exhibits an exothermic reaction so as to avoid thermal excursions at or exceeding the devitrification temperature of the composition of the bioactive glass of the fiber 210 and/or any bonding agents 220. The bioactivity of the fiber 210 and/or any bonding agents 220 maintained in an amorphous form will exhibit greater bioactivity, i.e., increased rate of resorption when implanted, to permit bone tissue ingrowth through the structural region 100 that can be offset by the reduction in porosity and/or a reduction in a pore size in the region. The bioactivity of the structural region 100 as determined by the compositional bioactivity and the pore morphology of the material must maintain the intervertebral space until such time as fusion between the vertebra occurs.

The structural region 100 in a bioactive glass composition having porosity in the range that provides sufficient strength when implanted and strength retention during fusion can be fabricated through various other modifications of the method 200 described above with reference to the glass-ceramic exemplary embodiment of FIG. 1. The porosity is controlled through variation of controllable variables including the diameter and length of the fiber 210, the relative quantity and particle size of the bonding agent 220, the relative quantity of the binder 230, and the particle size and quantity of the pore former 240. Furthermore, processing variables such as heating rate, temperature, and duration can influence the resulting porosity of the formed object during the method 200. Additionally, the bonding agent 220 can be eliminated and/or the mixing parameters such as time and speed can be increased to further chop the fibers to reduce the distribution of fiber length in the mixture. In an exemplary embodiment the reduction of porosity of the structural region 100 in a bioactive glass composition to provide high strength is attained through an extended duration in the reaction formation step 330 to densify the porous structure once the fiber bonds are formed.

Referring back to FIG. 1, the formed object of the glass-ceramic or glass composition is machined into a shape having dimensions sufficient to maintain the intervertebral space once implanted to form a first spinal interbody device 10. The first spinal interbody device 10 can include a central cavity 20 into which autograft or allograft can be inserted during the operational procedure implanting the intervertebral device 10.

Figure 2:
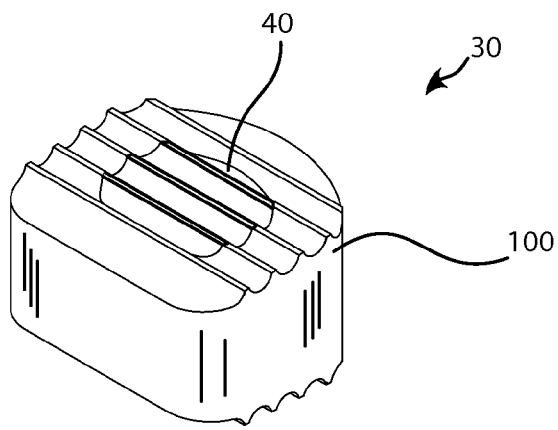
FIG. 2 shows a second spinal interbody device according to an embodiment of the present invention.

Referring to FIG. 2, in a second exemplary embodiment a second spinal interbody device 30 is shown for use in fusion of adjacent vertebrae to maintain the intervertebral spacing as bone tissue fuses the adjacent vertebrae. In this embodiment the structural region 100 of the first spinal interbody device 10 according to FIG. 1 is used with the central cavity 20 of the first spinal interbody device 10 in either of a bioactive glass or a glass-ceramic composition filled with a porous bioactive glass region 40. In this embodiment the porous bioactive glass region 40 has an increased level of bioactivity compared to the bioactivity of the structural region 100 due to the bioactivity of amorphous bioactive glass and/or increased porosity relative to the structural region 100.

The porous bioactive glass region 40 of the second exemplary embodiment can be fabricated using the same method 200 described above with reference to the first exemplary embodiment of FIG. 1 with specific modifications to the process to ensure the formed object maintains the amorphous glass composition of the bioactive fiber 200. A first modification to the process of the method 200 can be implemented by reducing or eliminating the use of a pore former 240 that exhibits an exothermic reaction so as to avoid thermal excursions at or exceeding the devitrification temperature of the composition of the bioactive glass of the fiber 210 and/or any bonding agents 220. The bioactivity of the fiber 210 and/or any bonding agents 220 maintained in an amorphous form will exhibit greater bioactivity, i.e., increased rate of resorption when implanted, to permit bone tissue ingrowth through the space occupied by the porous bioactive glass region 40. This accelerated ingrowth will effectuate fusion of the adjacent vertebrae before the structural region 100 is resorbed, thereby permitting the structural region to provide load bearing support and maintain the intervertebral spacing until such time that fusion has occurred. The porous bioactive region provides a similar function as autograft without the need to harvest the graft tissue, or allograft without the complications and potential risks of using cadaver tissue.

The porous bioactive glass region 40 can be fabricated as a formed object in a process as disclosed above and then machined into a shape that is inserted into a central cavity of the structural region 100. Alternatively, the porous bioactive glass region 40 can be fabricated by creating a plastic mixture of the batch material as disclosed above that is pressed into the central cavity of the structural region that is then heat treated to form a rigid amorphous porous structure, followed by machining, if necessary, to remove excess material to provide a rigid form adhered and contained within the region 40.

Alternatively, and not shown in FIG. 2, the second exemplary embodiment can be adapted to provide a structural region 100 in the central cavity of the interbody device 30 with the porous region 40 in the outer peripheral region of the interbody device 30. In this embodiment the porous region 40 will resorb and stimulate ingrowth between opposing vertebral bodies more rapidly than the central region to effectuate fusion of the adjacent vertebrae.

Figure 3:
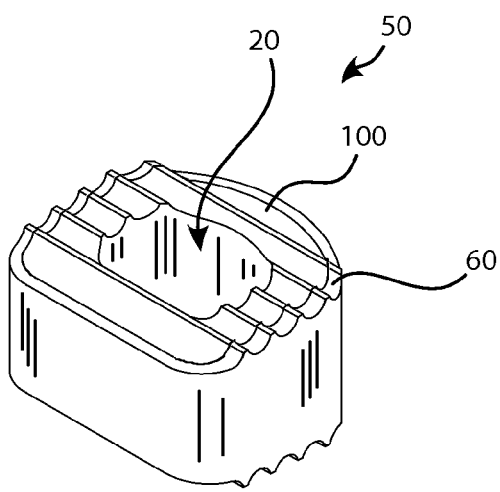
FIG. 3 shows a third spinal interbody device according to an embodiment of the present invention.

Referring to FIG. 3, in a third exemplary embodiment a third spinal interbody device 50 is shown for use in fusion of adjacent vertebrae to maintain the intervertebral spacing as bone tissue fuses the adjacent vertebrae. In this embodiment a structural region 100 is formed with a central cavity in a bioactive glass or glass-ceramic composition as disclosed above according to the method 100 described with reference to the embodiments of FIG. 1. In a series of subsequent processing steps a plastic batch mixture of the same, or similar composition of bioactive fiber 210 is created according to the method 100 described above with the selection of pore former 240 being made so as to reduce or eliminate the potential for an exothermic reaction during pore former removal so as to maintain the amorphous form of the fiber 210 and/or any bonding agent 220. The plastic batch material is then applied to the exterior circumferential face of the structural region 100 and then cured to form a porous bioactive glass outer region 60.

The porous bioactive glass outer region 60 of the third exemplary embodiment is cured into a rigid form and adhered to the exterior circumferential face of the structural region 100 in a manner similar to the curing of the bioactive glass region 40 of the embodiment disclosed with reference to FIG. 2. Specific modifications are made to ensure the bioactive glass outer region 60 maintains an amorphous form by preventing thermal excursions at or exceeding the devitrification temperature of the composition of the fiber 210 and/or any bonding agent 220. The bioactivity of the fiber 210 and/or any bonding agents 220 when in its original amorphous form, will exhibit a comparatively higher level of bioactivity and thus resorb by the body at a faster rate than the glass ceramic composition of the structural region or the low porosity form of the structural region having a bioactive glass composition and thus, advance tissue ingrowth around the exterior circumferential region of the implant, thereby promoting fusion of the adjacent vertebrae while the structural region 100 can continue to maintain the intervertebral spacing and address load bearing forces. When implanted, the central cavity 20 can be empty or filled with autograft, allograft, or other synthetic bone graft materials to promote fusion through tissue ingrowth.

Figure 4:
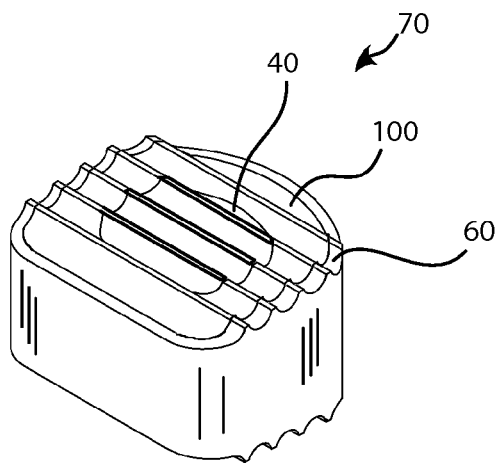
FIG. 4 shows a fourth spinal interbody device according to an embodiment of the present invention.

Referring to FIG. 4, in a fourth exemplary embodiment a fourth spinal interbody device 70 is shown for use in fusion of adjacent vertebrae to maintain the intervertebral spacing as bone tissue fuses the adjacent vertebrae. In this embodiment the spinal third spinal interbody device 50 with a porous bioactive glass outer region 60 as disclosed with reference to FIG. 3 is used with the bioactive glass region 40 in the central cavity of the structural region 100 as disclosed above with reference to FIG. 2. Once implanted between adjacent vertebrae the high level of bioactivity of the bioactive glass region 40 and the bioactive glass outer region 60 of the fourth spinal intervertebral device 70 will promote bone tissue ingrowth through the central cavity of the structural region 100 and advance tissue ingrowth around the exterior circumferential region of the implant. In this manner the fourth spinal interbody device 70 can effectuate fusion of the adjacent vertebrae while the structural region 100, with its comparatively lower level of bioactivity and/or lower porosity through reduced pore size and interconnectedness, and thus resorption, will continue to provide load bearing support and maintain the intervertebral spacing wile the bone matures into healthy and mature bone tissue for a safe and effective fusion. Ultimately, in each of the embodiments according to FIG. 1, FIG. 2, FIG. 3, and FIG. 4 the structural region will resorb, albeit relatively slowly, with mature bone maintaining the intervertebral space and load, leaving a fused vertebrae with no trace of an implant or spacer.

Figure 6:
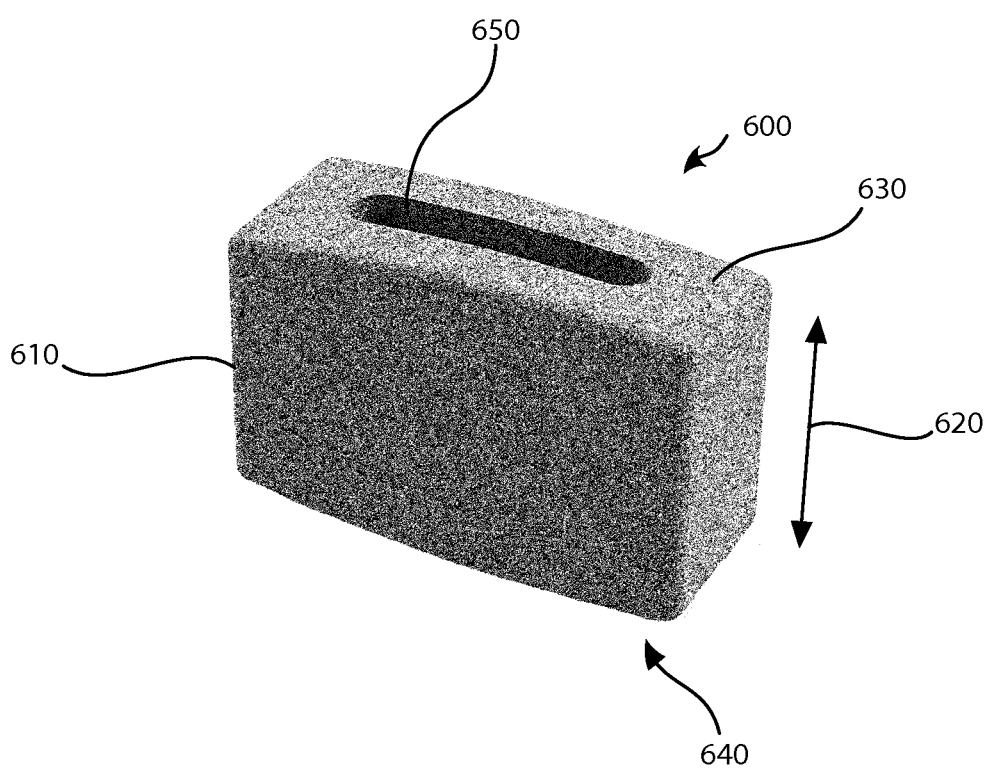
FIG. 6 depicts the design of an embodiment of the present invention that can be implanted as an intervertebral body in a degenerative disc disease procedure for interbody fusion.

Referring to FIG. 6, the design of an embodiment of the present invention is shown that can be implanted as an intervertebral body in a degenerative disc disease procedure for interbody fusion. The implant 600 has a first end surface 630 at a proximal end and a second end surface 640 at a distal end of the body with a body height 620. The implant 600 has a body wall 610 and a central cavity 650 extending from the first surface 630 to the second surface 640. As described above with reference to FIG. 1, FIG. 2, FIG. 3, and FIG. 4, a structural region can be provided that extends from the first surface 630 to the second surface 640 and a porous region from the first surface 630 to the second surface 640, each of the structural region and the porous region will resorb, albeit relatively slowly, with mature bone maintaining the intervertebral space and load, leaving a fused vertebrae with no trace of the implant 600.

EXAMPLES

The first spinal interbody device 10 can be fabricated as follows. 100 grams of silica calcium phosphate glass fiber in an amorphous composition generally known as 13-93 in chopped form having an average diameter of 30 μm is mixed with 25 grams HPMC as the binder 230, 75 grams PMMA having a particle size resulting from sieving in a 30-50 mesh (297 μm-595 μm) and 12.5 grams graphite powder having a particle size resulting from sieving in a 40-100 mesh (149 μm-400 μm), collectively as the pore former, 12.5 grams 13-93 glass material finely ground in powder form as a bonding agent 220, and 100 ml water. Once mixed into a plastic batch material and formed into an approximately 35 mm cube form and dried in a 90° C. oven for 16 hours. The dried block is then subjected to heat treatment raising to 900° C. for 30 minutes. The graphite pore former is observed to burn out to rapidly increase the internal temperature of the block during the heat treatment cycle to promote the formation of a wollastonite in a glass-ceramic composition. The block is then machined into the shape 600 as shown in FIG. 6 and then heat treated at 720° C. for 10 hours to promote further crystallization of the structural region and exhibiting a porosity of approximately 55% with a compressive strength of about 55 MPa.

The first spinal interbody device 10 can alternatively be fabricated as follows. A porous bioactive material having an amorphous composition is fabricated by mixing 100 grams of chopped 13-93 fiber having a diameter of 30 μm with 25 grams HPMC as the binder, 50 grams PMMA having a particle size resulting from sieving in a 40-50 mesh as the pore former, 12.5 grams 13-93 glass material as the bonding agent with 90 ml water, into a homogeneous mixture. The homogeneous mixture is then formed into a block and heat treated by raising the temperature to 660° C. for 2 hours with 10 SCFH air flow to form a porous amorphous bioactive glass material. The block is then machined into the shape 600 as shown in FIG. 6. The porous bioactive material will exhibit a porosity of approximately 45% with a compressive strength of about 35 MPa.

The second spinal interbody device 30 can be fabricated as follows. A porous bioactive material having an amorphous composition is fabricated by mixing 100 grams of chopped 13-93 fiber having a diameter of 30 μm with 25 grams HPMC as the binder, 50 grams PMMA having a particle size resulting from sieving in a 40-50 mesh as the pore former, 12.5 grams 13-93 glass material as the bonding agent with 90 ml water, into a homogeneous mixture. The homogeneous mixture is then formed into a block and heat treated by raising the temperature to 650° C. for 1.5 hours with 10 SCFH air flow to form a porous amorphous bioactive glass material. This material is then machined into a shape that can fit within the central cavity of the first spinal interbody device 10 in either the glass-ceramic or alternative amorphous composition, with a final machining operation to clean excess material. The amorphous material 40 in this example has a porosity of about 59% with a compressive strength of 12 MPa.

The third spinal interbody device 50 can be fabricated as follows. A first spinal interbody device 10 in the glass-ceramic or alternative amorphous composition is provided with approximately 20% of the outer circumferential material removed by machining. The homogeneous mixture of the second interbody device 30 is then spread to form an outer layer and then heat treated by raising the temperature to 650° C. for 1.5 hours with 10 SCFH air flow to form a porous amorphous bioactive glass material on the outer circumferential surface of the device. The first spinal interbody device 10 can be placed centrally in a cylinder with the homogeneous mixture pressed in to surround the device. Once dried and heat treated in accordance with the procedure above with reference to the porous amorphous glass material of the second spinal interbody device 30 above, the third spinal interbody device 50 is provided. A final machining process can be performed to remove excess material using the central cavity for orientation.

The fourth spinal interbody device 70 can be fabricated as follows. The the porous amorphous glass material machined into the shape of the central cavity, as disclosed above with reference to the second spinal interbody device 30 above is inserted into the central cavity of the third spinal interbody device 50 as described above. A final machining step can be performed to remove any excess material.

The present invention has been herein described in detail with respect to certain illustrative and specific embodiments thereof, and it should not be considered limited to such, as numerous modifications are possible without departing from the spirit and scope of the appended claims.

What is claimed is:

1. A spinal interbody implantable device comprising:
 a body having a first end surface at a proximal end of the body and a second end surface opposite thereto at a distal end of the body, the body extending between the first and second surfaces to define opposing top and bottom vertebral engaging surfaces, the body further defining side surfaces, the distance between the first and second surfaces defining a height of the body;
 the body having a structural region extending from the first surface to the second surface and composed essentially of a porous bioactive glass material having an anatomic load bearing strength in the human spine, the structural region having a first level of bioactivity;
 the body having a porous region extending from the first surface to the second surface, the porous region having a second level of bioactivity;
 the second level of bioactivity being greater than the first level of bioactivity;
 the structural region and the porous region each exhibiting resorption when implanted in human tissue; and
 the body being adapted to be inserted into the space between adjacent vertebrae associated with the height wherein an ingrowth of tissue responsive to the respective first level of bioactivity and the second level of bioactivity promotes fusion.

2. The spinal interbody implantable device according to claim 1 wherein the porous region is located in a central cavity of the body.

3. The spinal interbody implantable device according to claim 1 wherein the structural region is an amorphous bioactive glass.

4. The spinal interbody implantable device according to claim 1 wherein the porous region is an amorphous bioactive glass.

5. The spinal interbody implantable device according to claim 1 wherein the structural region is a silica glass.

6. The spinal interbody implantable device according to claim 1 wherein the structural region is a phosphate glass.

7. The spinal interbody implantable device according to claim 1 wherein the structural region is a glass-ceramic and the porous region is an amorphous glass.

8. The spinal interbody implantable device according to claim 1 wherein the structural region is located in a central cavity of the body.

9. The spinal interbody implantable device according to claim 1 further comprising a second porous region extending from the first surface to the second surface, the second porous region having a third level of bioactivity, the second porous region exhibiting resorption when implanted in human tissue.

10. The spinal interbody implantable device according to claim 9 wherein the second porous region is located on an outer peripheral surface of the body.

11. The spinal interbody implantable device according to claim 9 wherein the third level of bioactivity is greater than the first level of bioactivity.

12. The spinal interbody implantable device according to claim 9 wherein the second porous region has a composition that is the same as a composition of the porous region.

13. A spinal interbody implantable device comprising:
a body having a first end surface at a proximal end of the body and a second end surface opposite thereto at a distal end of the body, the distance between the first surface and the second surface defining a height of the body;
the body having a first region extending from the first surface to the second surface and composed of bioactive glass fiber bonded into a structure of interconnected pores, the first region having a first porosity;
the body having a second region extending from the first surface to the second surface, the second region composed essentially of a bioactive glass fiber bonded into a structure of interconnected pores, the second region having a second porosity, the second porosity being greater than the first porosity; and
the body being adapted to be inserted into the space between adjacent vertebrae associated with the height having contact with opposing vertebral surfaces wherein an ingrowth of tissue responsive to the respective first porosity and the second porosity promotes fusion.

14. The spinal interbody implantable device according to claim 13 wherein the first region is located in a central cavity of the body.

15. The spinal interbody implantable device according to claim 13 wherein the first region is an amorphous bioactive glass.

16. The spinal interbody implantable device according to claim 13 wherein the second region is an amorphous bioactive glass.

17. The spinal interbody implantable device according to claim 13 wherein the first region is a silica glass.

18. The spinal interbody implantable device according to claim 13 wherein the first region is a phosphate glass.

19. The spinal interbody implantable device according to claim 13 wherein the first region is a glass-ceramic and the second region is an amorphous glass.

20. The spinal interbody implantable device according to claim 13 further comprising a third region extending from the first surface to the second surface, the third region having a third level of porosity, the third region exhibiting resorption when implanted in human tissue.

21. The spinal interbody implantable device according to claim 20 wherein the third region is located on an outer peripheral surface of the body.

* * * * *